United States Patent
Cozzi

(10) Patent No.: US 6,579,094 B2
(45) Date of Patent: Jun. 17, 2003

(54) DENTAL INSTRUMENT WITH MACHINED HANDLE AND METHOD FOR FORMING

(76) Inventor: Gualtiero Cozzi, Via Francesco Nullo, 13, I-50137 Firenze (IT)

( * ) Notice: Subject to any disclaimer, the term of this patent is extended or adjusted under 35 U.S.C. 154(b) by 44 days.

(21) Appl. No.: 09/883,905

(22) Filed: Jun. 18, 2001

(65) Prior Publication Data

US 2001/0031444 A1 Oct. 18, 2001

Related U.S. Application Data

(63) Continuation of application No. 09/360,238, filed on Jul. 23, 1999, which is a continuation-in-part of application No. 09/079,127, filed on May 25, 1999, now abandoned, which is a continuation of application No. 08/737,186, filed on Jan. 3, 1997, now abandoned.

(30) Foreign Application Priority Data

May 5, 1994 (IT) .......................................... FI940047 U
May 2, 1995 (WO) ................................. PCT/IT95/00065

(51) Int. Cl.$^7$ ................................................. A61C 3/00
(52) U.S. Cl. ........................ 433/141; 451/28; 81/177.1
(58) Field of Search ................................. 433/141, 142, 433/143, 144, 145, 146, 147, 148, 149, 150, 152, 163, 164; 451/28; 81/177.1

(56) References Cited

U.S. PATENT DOCUMENTS

| | | | |
|---|---|---|---|
| 4,723,582 A | * 2/1988 | Caspall | ...................... 81/177.1 |
| 5,004,419 A | * 4/1991 | Kline | .......................... 433/143 |
| 5,271,135 A | * 12/1993 | Shifferly | ........................ 29/78 |
| 5,624,259 A | * 4/1997 | Heath et al. | ................. 433/141 |

* cited by examiner

Primary Examiner—John J. Wilson
(74) Attorney, Agent, or Firm—McGlew and Tuttle, P.C.

(57) ABSTRACT

A dental use instrument having a handle and a functional element connected to one end of the handle. The functional element is used to perform a dental procedure. A portion of the handle, and preferably the entire handle has a surface which is treated by satinizing, which produces a uniform surface roughness in the form of a plurality of microchannels which a circumferential directional component. The magnitude of the plurality of micro channels is of a size to provide a surface free of indentations. In an alternative embodiment, a functional element is connected to each end of the handle, and the surface roughness is provided on the surface of the handle at each end.

19 Claims, 3 Drawing Sheets

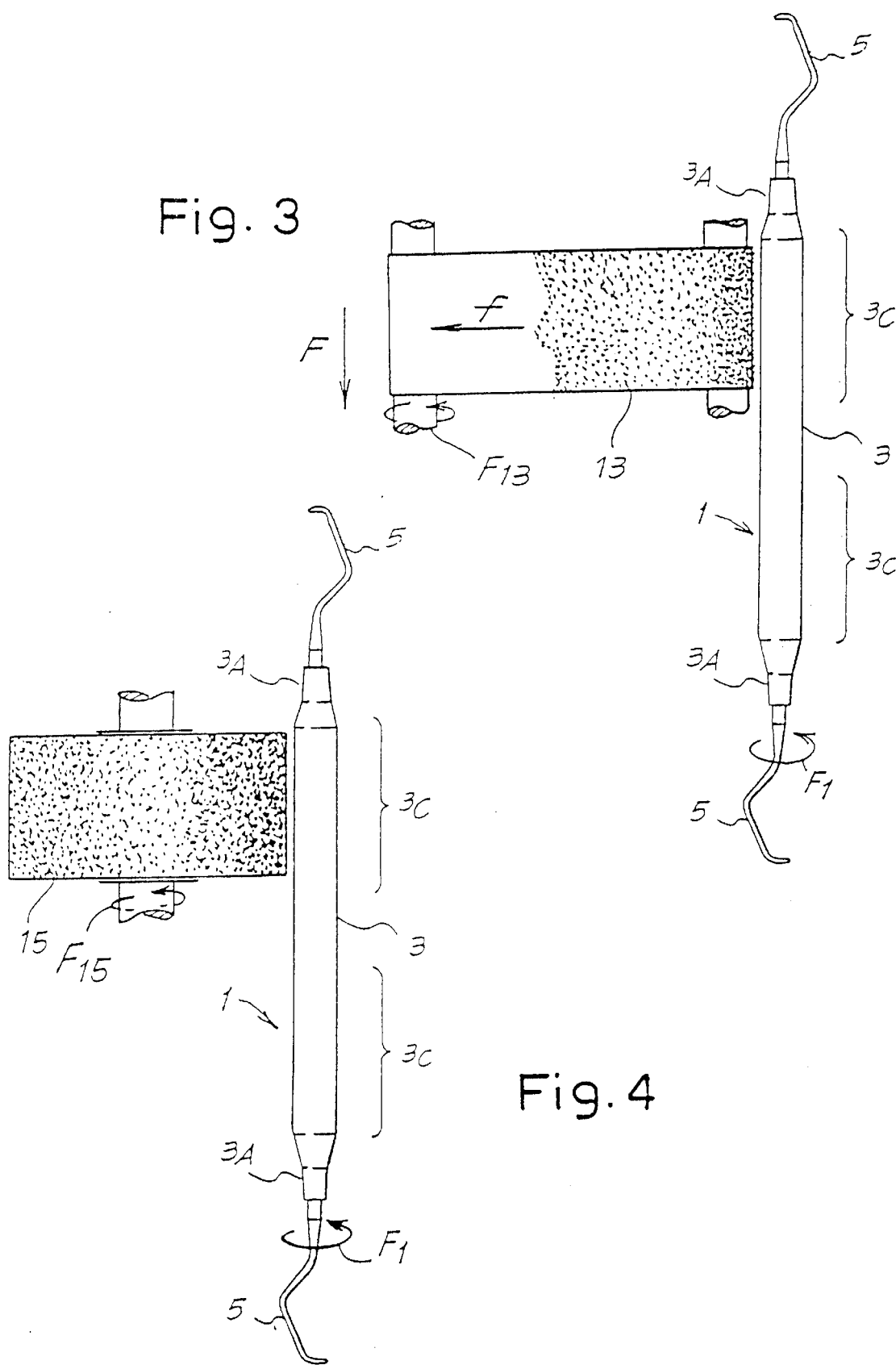

Fig. 5
Fig. 6
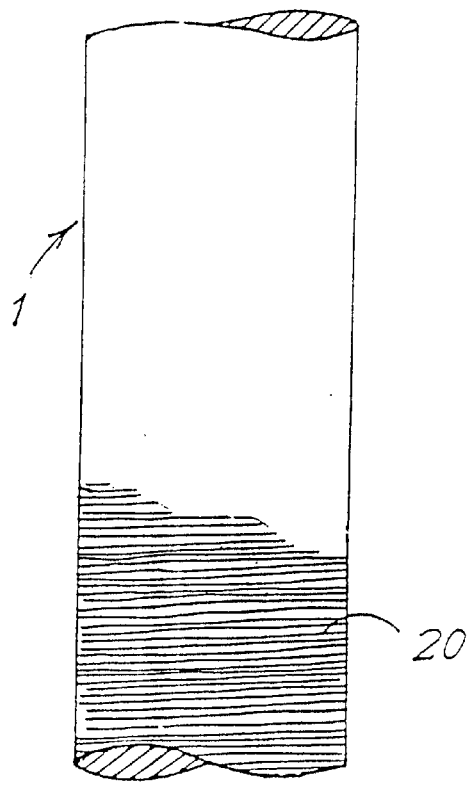
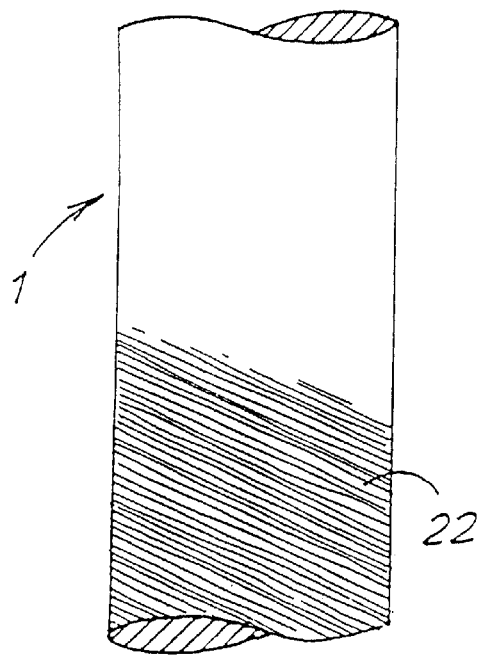

DENTAL INSTRUMENT WITH MACHINED HANDLE AND METHOD FOR FORMING

RELATED APPLICATIONS

This is a Continuation of application Ser. No. 09/360,238 filed Jul. 23, 1999, which is a continuation-in-part of Ser. No. 09/079,127 filed May 25, 1999, now abandoned which is a continuation of Ser. No. 08/737,186 filed Jan. 3, 1997 now abandoned and the entire disclosure of this prior application is considered to be part of the disclosure of the accompanying application and is hereby incorporated by reference therein.

FIELD OF THE INVENTION

The invention relates to an instrument for dental use, of the type comprising a handle and one or two active ends that are pointed or variously shaped for use in various types of procedures, and in particular to a specific type of finish on the handle and a method of forming the finish.

BACKGROUND OF THE INVENTION

Currently known instruments of this type have a handle of which a portion has a knurled or ridged surface, in particular a knurled surface with deep indentations. The portion of the surface machined in this way is currently thought to be necessary to enable the dentist to have a firm grip on the instrument.

The knurling, while considered necessary for gripping the instrument, has proved to be a source of major disadvantages, particularly with regard to hygiene. The indentations in the knurled surface trap contaminants and dirt that could transmit microorganisms. Although they are sterilized, instruments of this type may not be perfectly cleaned because contaminants can accumulate in the indentations in the knurled surface.

SUMMARY AND OBJECTS OF THE INVENTION

The primary object of the present invention is a surgical instrument, particularly intended for dental use and method of making same, which does not have the above disadvantages but nevertheless still has the advantage of enabling the dentist to grip the instrument correctly and firmly.

The instrument according to the present invention is substantially characterized in that the handle is substantially smooth and has at least one grip zone which has a plurality of microchannels extending in a circumferential direction of the handle. The plurality of microchannels form a uniform surface roughness with the microchannels being arranged on the handle in a uniform random distribution. Each of the micro-channels are sized to be below a magnitude to collect contaminants. The grip zone is formed by providing a grinding surface with a magnitude of roughness that is below a roughness to cause indentations in the handle that would collect contaminants. A grinding surface in the form sandpaper having a grade or sieve number between n. 105 and 500 of the US standard sieves scale is used to create the micro-channels. Sandpaper of n. 240 grade has been found to the most desirable. Other grinding surfaces and other devices can also be used which form the same type of uniform random distribution of microchannels as formed by sandpaper having a grade between n. 105 and n. 500 of the US standard sieves scale. The functional element of the instrument is connected to one of the ends of the handle for performing a dental procedure. The grinding surface is rotated relative to an outer surface of the handle and the handle is held against the grinding surface to form micro-channels in the handle. The relative rotating has a directional component in a circumferential direction of the handle. The micro-channels thus formed are of a size being below a magnitude to collect contaminants. The relative rotating forms the micro-channels in the circumferential direction of the handle.

Alternatively, the outer surface of the handle is also moved against the grinding surface in an axial direction of the handle to also form the micro-channels in the handle. The axial moving is performed substantially simultaneously with the relative rotating to form the micro-channels in both the circumferential direction and the axial direction of the handle. This causes the micro-channels to be formed in a helicoidal direction of the handle.

This type of grip surface provides sufficient roughness to ensure that the user can grip it correctly, and that there is no need for indentations, cavities or other forms of uneven surface that could trap contaminants or pathogens. In the context of the present description the grinding surface covers any surface or device which forms a uniform random distribution of microchannels as formed by sandpaper having a grade between n. 104 and n. 500 of the US standard sieves scale. This size and distribution has been found to allow sufficient roughness to be obtained without the formation of indentations which could form a trap for contaminants or pathogens.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a second arrangement of a belt grinding device during machining of the handle of an instrument according to the invention;

FIG. 4 is a third arrangement of a grinding device during machining of the handle of an instrument according to the invention;

FIG. 5 is a schematic view of an enlarged portion of the handle of FIG. 1 in a first embodiment;

FIG. 6 is a schematic view of an enlarged portion of the handle of FIG. 1 in a second embodiment;

DESCRIPTION OF THE PREFERRED EMBODIMENT

Figure 1:
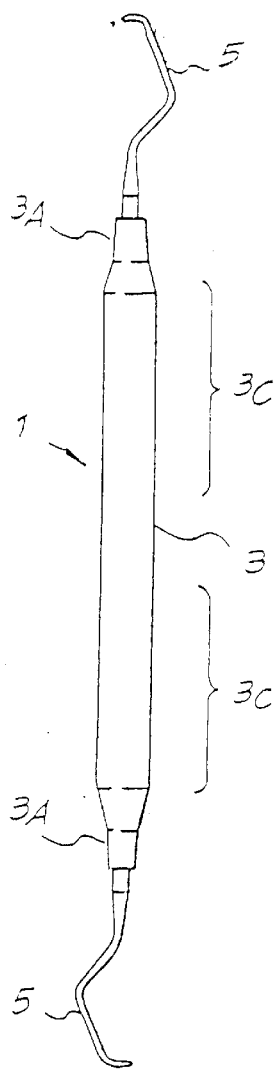
FIG. 1 is a side view of an instrument according to the invention.

Referring to the drawings, the instrument generically illustrated by 1 and made of steel or another suitable material has a central handle zone 3 with ends 3a which are provided with two parts 5 which constitute the functional elements of the instrument. The parts 5 are generally almost symmetrical and can be of any shape. In dentistry, various shapes of instruments are known for the various procedures that have to be performed. The present invention can be applied indiscriminately to any type of instrument with the general structure illustrated in the FIG. 1, apart from the shape of the parts 5, the size and the shape of the cross-section of the handle.

Characteristically, the central zone of the handle 3 has a particular grip surface. In the example illustrated the entire surface of the handle 3 is covered with the grip zone, but it is clearly sufficient to provide the grip zone to those portions 3C of the handle that are gripped by the dentist.

Figure 2:
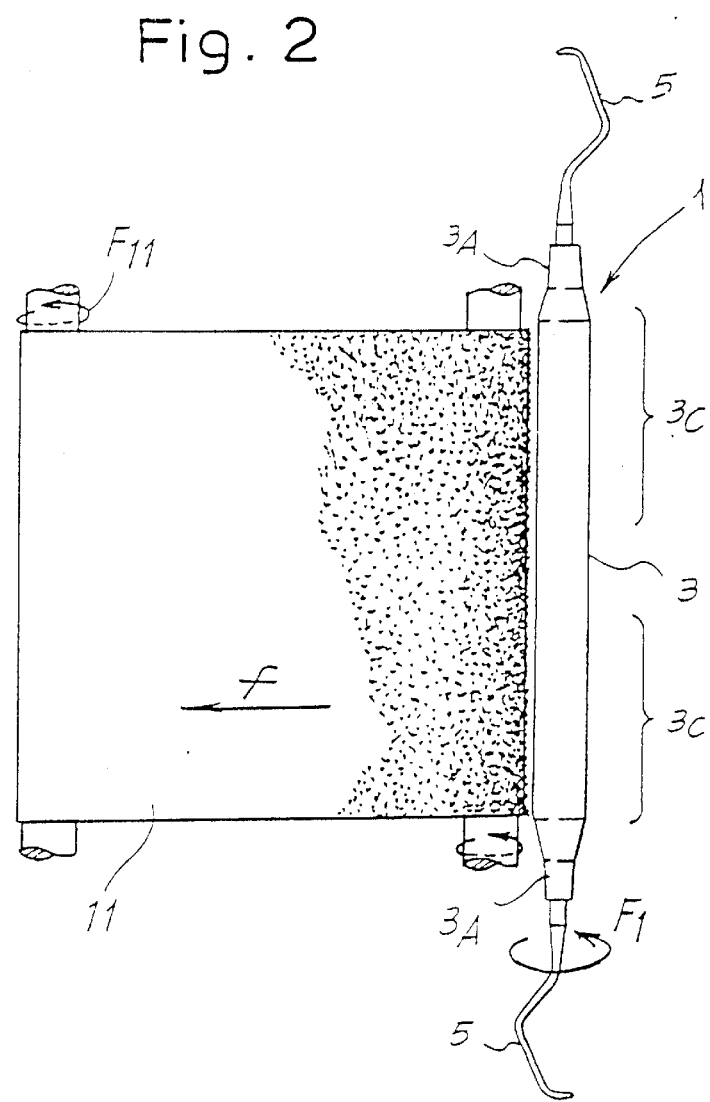
FIG. 2 is a first arrangement of a belt grinding device during machining of the handle of an instrument according to the invention.

FIG. 2 shows a first arrangement of a belt grinding device for machining the handle of the instrument according to the invention. An abrasive belt, such as a belt made of abrasive paper with a grinding surface of sufficiently fine roughness, labeled 11, is trained around two rollers having parallel axes. The magnitude of roughness of the grinding surface is below a roughness to cause indentations in the handle that would collect contaminants. An abrasive belt formed of sandpaper within a grade or sieve number range of n. 105 and n. 500 of the US standard sieves scale has been found to be sufficient. Sandpaper of grade n. 240 has been found to be most desirable for dental use.

One of the rollers is motorized and rotates according to arrow $F_{11}$. This causes the belt to move along the direction of arrow f. The instrument 3 is brought into contact with belt 11. The width of the belt is substantially the same as the length of the handle 33, or at least of the portion of the handle which is requested to be satinized or finished.

Machining of the handle is obtained by slowly rotating the handle around its axis according to arrow $F_1$, while belt 11 is moving according to arrow f. A textured surface is thus obtained on handle 3. The texture has a substantially circumferential orientation, as schematically shown in FIG. 5. Micro-channels are machined by the abrading granules of belt 11. The granules are of very fine granulometry, such that the texture on the surface of handle 3 is such as not to generate cavities in which dirt or microorganisms can be trapped.

The coefficient of friction of such a surface is less than that of commonly used indented surfaces of similar handles. However, a sufficient grip is ensured by the particular orientation of the texture on the surface of the handle. The circumferential orientation of the texture is such as to give the highest coefficient of friction in the axial direction, i.e. in the direction in which the force is exerted by the dentist during use of the handle.

FIG. 3 shows a similar arrangement, wherein the abrasive belt 13 has width which is less than the length of the axial extension of the handle surface to be machined. Inn this case an additional axial motion along axis F can be imparted to belt 13 while machining the handle. The result is a texture in the form of helicoidal microchannels, as diagrammatically shown in FIG. 6 by texture or finish 22. The inclination of the helicoidal channels is dependent upon the ratio between the rotation speed of the handle, arrow $F_1$, and the translation speed of belt 13, arrow F. If a sufficiently low speed is used for the motion in the direction of arrow F, the inclination of the microchannels is such as to ensure sufficient grip in the axial direction.

FIG. 4 shows an embodiment in which a metal working tool such as a rotating cylindrical tool 15 is used instead of an abrading belt. The abrasiveness of the rotating cylindrical tool 15 is chosen to cause a size of the plurality of micro-channels to be equivalent to micro-channels formed from abrasion by a sandpaper surface having a sandpaper grade between n. 105 and n. 500 of the US standard sieves scale. Other metal working tools are also possible, such as a brush having metal bristles being forced against the handle during rotation of the handle.

The metal working tool, regardless of whether it is sandpaper, a rotating cylindrical tool, or a metal brush, has a randomizing structure to cause the micro-channels to be randomly positioned on the handle in a uniform random distribution. This randomizing structure can be in the form of a uniform random distribution of grit particles on the sandpaper or rotating cylindrical tool. This randomizing structure can also be in the form of a uniform random distribution of metal bristles on the brush, as well as randomizing collisions between the bristles themselves and against the handle when the metal brush is forced against the handle. Random motion between the tool and the handle is also possible.

Other tools, and other randomizing structure can be used within the scope of the present invention to produce a size of the micro-channels equivalent to micro-channels formed from abrasion by a sandpaper surface having a sandpaper grade between n. 105 and n. 500 of the US standard sieves scale, and to cause the micro-channels to be randomly positioned on the handle in a uniform random distribution.

While specific embodiments of the invention have been shown and described in detail to illustrate the application of the principles of the invention, it will be understood that the invention may be embodied otherwise without departing from such principles.

What is claimed is:

1. An instrument for dental use comprising:
   a handle with a surface;
   an active end connect to said handle, said active end having one of a pointed or shaped portion for use in a procedure, said handle surface being substantially smooth, said handle surface being formed by at least one of the steps of satinizing, sand blasting, sanding and shot blasting to create a plurality of micro-channels, said micro-channels having a size equivalent to micro-channels formed from abrasion by a sandpaper surface having sandpaper grade between sieve number 105 and sieve number 500 of the US standard sieves scale.

2. An instrument according to claim 1, wherein said entire surface of said handle is formed by one or more of satinizing, sand blasting, sanding and shot blasting.

3. An instrument according to claim 2, wherein said handle and active end are formed of metal including at least one of steel and aluminum.

4. A grip portion of a dental instrument formed by the process of:
   providing a handle of the dental instrument;
   applying a sanding surface to said handle using a sanding surface with a sanding surface grade between sieve number 105 and sieve number 500 of the US standard sieves scale grade; and
   relatively rotating an outer surface of said handle during said step of satinizing, sand blasting or shot blasting said handle to form micro-channels in said handle and create a substantially smooth continuous textured surface of uniform roughness completely around said handle with said micro-channels randomly positioned on said handle in a uniform random distribution, said relative rotating having a directional component in a circumferential direction of said handle.

5. A method for forming a grip portion on a dental instrument, the method comprising the steps of:
   providing a handle of the dental instrument;
   providing metal working material for abrading a surface of the handle;

relatively rotating an outer surface of said handle with respect to said metal working tool;

forcing said metal working material against said handle to form micro-channels in said handle and create a substantially smooth continuous textured surface of uniform roughness completely around said handle, said step of forcing forming said micro-channels randomly positioned on said handle in a uniform random distribution, a size of said plurality of micro-channels being equivalent to micro-channels formed from abrasion by a sanding surface having a sanding grade between sieve number 105 and sieve number 500 of the US standard sieves scale.

6. A method in accordance with claim 5, wherein:

said relative rotating forms said micro-channels in said circumferential direction of said handle.

7. A method in accordance with claim 5, further comprising:

axially moving said outer surface of said handle against said metal working tool in an axial direction of said handle to also form said micro-channels in said handle, said axial moving being performed substantially simultaneously with said relative rotating, said axially moving and said relative rotating forming said micro-channels in both said circumferential direction and said axial direction of said handle.

8. A method in accordance with claim 7, wherein:

said micro-channels are formed in a helicoidal direction of said handle.

9. A method in accordance with claim 5, wherein:

said relative rotating forms said micro-channels in both said circumferential direction and an axial direction of said handle.

10. An instrument for dental use comprising:

a handle with a surface;

an active end connected to said handle, said active end having one of a pointed or shaped portion for use in a procedure, said handle surface being substantially smooth, said handle surface being formed by at least one of the steps of satinizing, sand blasting, sanding and shot blasting, said handle having opposite ends and a substantially smooth outside surface with a plurality of micro-channels extending in substantially in a circumferential direction of said handle, said plurality of micro-channels being randomly positioned on said handle in a uniform random distribution, said plurality of micro-channels being formed by said one of satinizing, sand blasting, sanding and shot blasting to provide said plurality of micro-channels with a size equivalent to micro-channels formed from abrasion by a sandpaper surface having a sandpaper grade between sieve number 105 and sieve number 500 of the US standard sieves scale; and said active end is connected to one of said opposite ends of said handle, said active end pointed or shaped portion being provided for use in a dental procedure.

11. An instrument in accordance claim 10 wherein:

said plurality of micro-channels have a size equivalent to micro-channels formed from abrasion by a sandpaper surface having a sandpaper grade of sieve number 240 of the US standard sieves scale.

12. An instrument in accordance with claim 10 wherein:

said plurality of micro-channel also extend in an axial direction to form a helicoidal pattern.

13. An instrument in accordance with claim 10, wherein:

said substantially smooth outside surface has a uniform surface roughness free of indentations and cavities.

14. An instrument in accordance with claim 10, wherein:

said handle is formed steel.

15. An instrument according to claim 10, wherein said entire surface of said handle is formed by one or more of satinizing, sand blasting, sanding and shot blasting.

16. A method for forming a grip portion on a dental instrument, the method comprising the steps of:

providing a handle of the dental instrument;

providing metal working material for abrading a surface of the handle;

relatively rotating an outer surface of said handle with respect to said metal working tool;

forcing said metal working material against said handle to form micro-channels in said handle and create a substantially smooth continuous textured surface of uniform roughness completely around said handle, said step of forcing forming said micro-channels randomly positioned on said handle in a uniform random distribution, a size of said plurality of micro-channels being equivalent to micro-channels formed from abrasion by a sanding surface having a sanding grade between sieve number 105 and sieve number 500 of the US standard sieves scale, said relative rotating having a directional component in a circumferential direction of said handle, and said metal working tool is a sanding surface having a grade between sieve number 105 and sieve number 500 of the US standard sieves scale.

17. A method in accordance with claim 16, wherein:

said sanding surface has a grade of sieve number 240 of the US standard sieves scale.

18. A method for forming a grip portion on a dental instrument, the method comprising the steps of:

providing a handle the dental instrument;

providing metal working material for abrading a surface of the handle;

relatively rotating an outer surface of said handle with respect to said metal working tool;

forcing said metal working material against said handle to form micro-channels in said handle and create a substantially smooth continuous textured surface of uniform roughness completely around said handle, said step of forcing forming said micro-channels randomly positioned on said handle a uniform random distribution, a size of said plurality of micro-channels being equivalent to micro-channels formed from abrasion by a sanding surface having a sanding grade between sieve number 105 and sieve number 500 of the US standard sieves scale, said relative rotating having a directional component in a circumferential direction of said handle and said metal working tool is a brush having metallic bristles.

19. A method for forming a grip portion on a dental instrument, the method comprising the steps of:

providing a handle of the dental instrument;

providing metal working material for abrading a surface of the handle;

relatively rotating an outer surface of said handle with respect to said metal working tool;

forcing said metal working material against said handle to form micro-channels in said handle and create a substantially smooth continuous textured surface of uniform roughness completely around said handle, said step of forcing forming said micro-channels randomly positioned on said handle in a uniform random distribution, a size of said plurality of micro-channels being equivalent to micro-channels formed from abrasion by a sanding surface having a sanding grade between sieve number 105 and sieve number 500 of the US standard sieves scale, said relative rotating having a directional component in a circumferential direction of said handle and said metal working tool is a rotating cylindrical tool.

* * * * *